(12) United States Patent
Thuemen et al.

(10) Patent No.: US 11,963,664 B2
(45) Date of Patent: Apr. 23, 2024

(54) ENDOSCOPE HAVING SUPPORT BODY WITH SEGMENTED ANNULAR SPACE

(71) Applicant: OLYMPUS Winter & Ibe GmbH, Hamburg (DE)

(72) Inventors: Alrun Thuemen, Hamburg (DE); Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 17/677,379

(22) Filed: Feb. 22, 2022

(65) Prior Publication Data
US 2022/0280030 A1    Sep. 8, 2022

(30) Foreign Application Priority Data

Mar. 4, 2021  (DE) .................... 10 2021 105 244.0

(51) Int. Cl.
*A61B 1/00*    (2006.01)
(52) U.S. Cl.
CPC ...... *A61B 1/00167* (2013.01); *A61B 1/00064* (2013.01); *A61B 1/00114* (2013.01)
(58) Field of Classification Search
CPC ............ A61B 1/00112; A61B 1/00117; A61B 1/00128; A61B 1/00114; A61B 1/00064; A61B 1/00167; A61B 1/00119; A61B 1/00105; A61B 1/07; A61B 1/00165; A61B 1/12; A61B 1/307; A61B 1/00052; A61B 1/00066; G02B 23/26; G02B 23/2469
See application file for complete search history.

(56) References Cited

U.S. PATENT DOCUMENTS

| 3,900,022 A | 8/1975 | Widran |
| 5,046,816 A * | 9/1991 | Lehmann ........... A61B 1/00165 |
| | | 385/115 |

(Continued)

FOREIGN PATENT DOCUMENTS

| DE | 39 29 285 A1 | 3/1991 |
| DE | 10 2019 100 144 A1 | 7/2020 |

(Continued)

OTHER PUBLICATIONS

German Office Action dated Sep. 8, 2021.

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

An endoscope including an elongated shaft. The elongated shaft including: an inner shaft tube in which an optical system is received; an outer shaft assembly including an outer shaft tube and a tubular support body proximally abutting the outer shaft tube; at least one bundle of optical fibers disposed between the inner shaft tube and the outer shaft tube; and an electrical connector arranged between the inner shaft tube and the support body. Where the support body includes at least a first web and a second web each extending radially between an inner surface of the support body and an outer surface of the inner shaft tube, the first web and the second web also extending in a longitudinal direction of the shaft such that an annular space between the inner shaft tube and the support body is divided into at least two segments.

17 Claims, 2 Drawing Sheets

(56) References Cited

U.S. PATENT DOCUMENTS

| | | | | |
|---|---|---|---|---|
| 5,179,620 A | * | 1/1993 | Hosaka | G02B 23/2446 |
| | | | | 385/119 |
| 6,547,724 B1 | * | 4/2003 | Soble | A61B 1/12 |
| | | | | 606/115 |
| 2005/0033319 A1 | * | 2/2005 | Gambale | A61B 17/0469 |
| | | | | 606/139 |
| 2005/0228452 A1 | * | 10/2005 | Mourlas | A61M 25/1002 |
| | | | | 606/41 |
| 2006/0041186 A1 | * | 2/2006 | Vancaillie | A61B 1/00135 |
| | | | | 600/128 |
| 2014/0257273 A1 | * | 9/2014 | Cosmescu | A61B 18/042 |
| | | | | 606/37 |
| 2016/0235286 A1 | * | 8/2016 | Chiang | A61B 1/00167 |
| 2021/0298591 A1 | * | 9/2021 | Jackson, III | A61B 1/0684 |

FOREIGN PATENT DOCUMENTS

| | | | | |
|---|---|---|---|---|
| EP | 2283768 A1 | * | 2/2011 | A61B 1/00064 |
| JP | 2001-017381 A | | 1/2001 | |
| JP | 2001017381 A | * | 1/2001 | A61B 1/00071 |
| WO | WO-2014158140 A1 | * | 10/2014 | A61B 1/0011 |

* cited by examiner

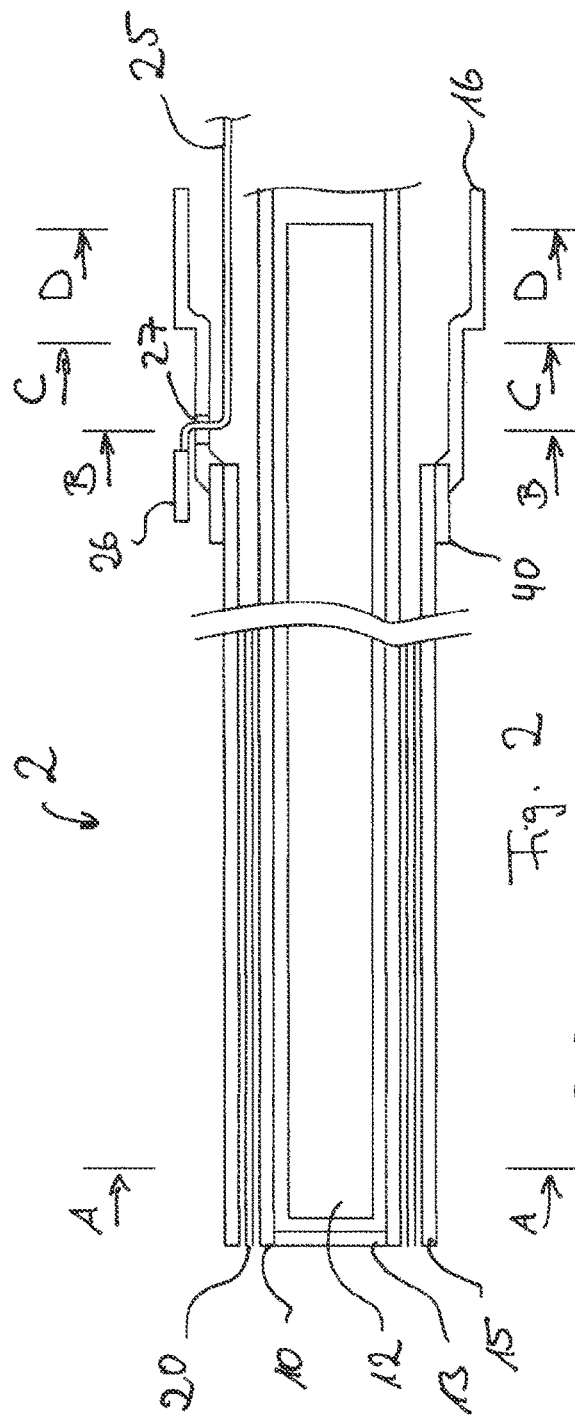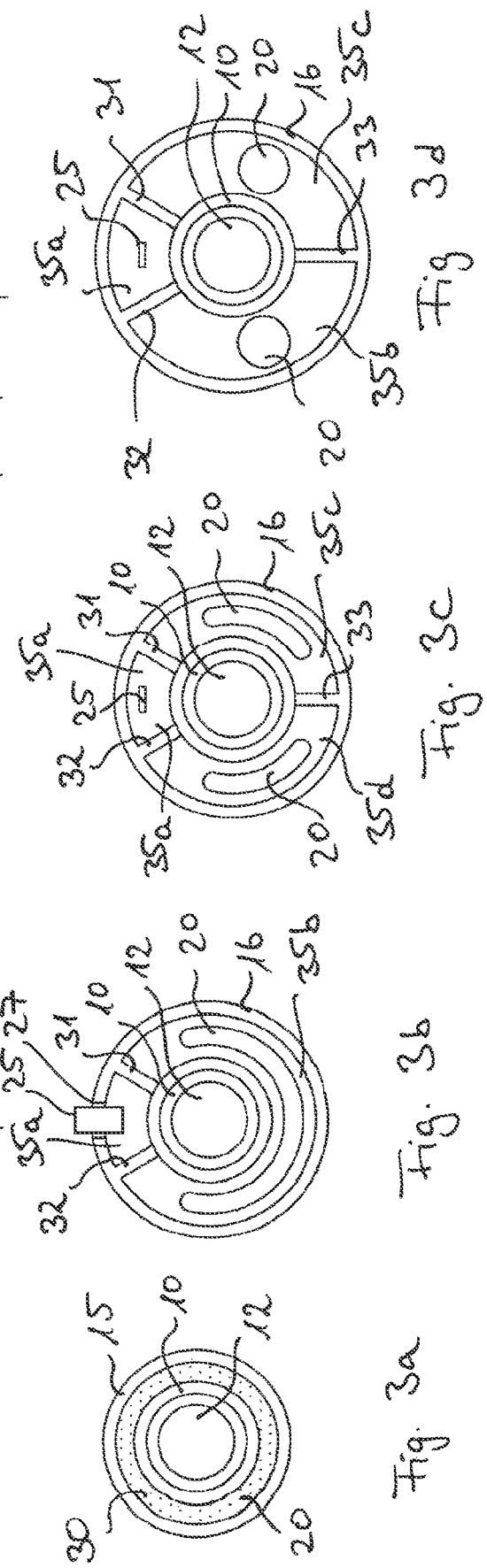

ENDOSCOPE HAVING SUPPORT BODY WITH SEGMENTED ANNULAR SPACE

CROSS-REFERENCE TO RELATED APPLICATION

The present application is based upon and claims the benefit of priority from DE 10 2021 105 244.0 filed on Mar. 4, 2021, the entire contents of which is incorporated herein by reference.

BACKGROUND

Field

The present disclosure relates to an endoscope and more particularly to an endoscope having an elongated shaft, comprising an inner shaft tube in which an optical system is received, and an outer shaft assembly comprising an outer shaft tube and a tubular support body proximally abutting the outer shaft tube, wherein at least one bundle of optical fibers is disposed between the inner shaft tube and the outer shaft tube, and an electrical connecting element is arranged between the inner shaft tube and the support body.

Prior Art

Endoscopes are used in medicine to examine and/or treat the interior of a body cavity of a patient. A basic distinction must be made between endoscopes with a flexible shaft and endoscopes with a rigid shaft.

The endoscopes with a rigid shaft of interest here generally comprise a shaft consisting of several shaft tubes extending into one another. In this regard, an inner shaft tube usually accommodates an optical system comprising an objective lens. The optical system may further comprise an electronic image converter converting an image generated by the objective lens into electronic video signals. The optical system may also comprise an optical image conductor which transmits the image produced by the objective lens along the shaft to an eyepiece at which it can be viewed by eye or recorded by a video camera.

The inner shaft tube is surrounded by an outer shaft assembly comprising an outer shaft tube and a tubular support body proximally abutting the outer shaft tube. The support body is usually made of metal and has a complex outer contour and associated with this, a significantly higher material thickness than the outer shaft tube. As a result, the support body has a relatively high weight, which can have a negative effect on the user-friendliness of the endoscope.

At least one bundle of optical fibers is arranged between the inner shaft tube and the outer shaft tube, with which illumination light is guided from a mostly external light source to a distal end of the shaft. At the distal end of the shaft, the inner shaft tube, the outer shaft tube, and the optical fibers are bonded together.

The adhesive distally hermetically seals an annular space between the shaft tubes. However, the adhesive bond is mechanically sensitive to forces that may act on the inner shaft tube during assembly of the endoscope. Such forces may cause cracking of the bond over the long lever of the inner shaft tube, compromising the hermetic seal.

When assembling the endoscope, the optical fibers must first be drawn in between the inner and outer shaft tubes before the electrical connecting element is inserted. During this process, the electrical connecting element may damage a protective tube of the optical fibers or the very sensitive optical fibers themselves. Therefore, great care must be taken when mounting the endoscope.

From DE 10 2019 100 144 A1, an endoscope is known in which a position-securing element is provided which supports the inner shaft tube in the outer shaft tube.

SUMMARY

An object is to provide an endoscope which is improved with respect to the problems described.

Such object can be achieved by an endoscope with an elongated shaft, comprising an inner shaft tube in which an optical system is received, and an outer shaft assembly comprising an outer shaft tube and a tubular support body proximally abutting the outer shaft tube, wherein at least one bundle of optical fibers is disposed between the inner shaft tube and the outer shaft tube, and an electrical connecting element is arranged between the inner shaft tube and the support body; which is further configured in that the support body comprises at least two webs extending in the direction of a longitudinal axis of the shaft, which webs divide an annular space formed between the inner shaft tube and the support body into at least two segments.

By dividing the annular space into two segments, it is possible to separate the optical fibers and the electrical connecting element from each other so that damage to the optical fibers is avoided when the connecting element is inserted.

The electrical connecting element may be guided through a first segment of the at least two segments. In this regard, the electrical connecting element may comprise a flexible printed circuit board and/or a cable. The at least one bundle of optical fibers may be arranged in a second segment of the at least two segments.

In an endoscope according to a further embodiment, the support body may comprise three webs which divide the annular space into three segments. In this regard, the endoscope may comprise at least two bundles of optical fibers, the second bundle of optical fibers being arranged in a third segment of the three segments.

One of the webs may be shorter in distal direction than the other webs, so that the second segment and the third segment converge to a common segment. This can simplify the merging of the bundles of optical fibers.

The webs may radially guide (position) the inner shaft tube. By guiding (positioning) the inner shaft tube radially, forces occurring during assembly can be absorbed by the webs so that they can no longer have a damaging effect on the distal bonding of the optical fibers.

The support body may comprise an injection-molded plastic body. A support body configured accordingly can be manufactured particularly efficiently and at the same time can be substantially lighter than a support body made of metallic material.

The support body may comprise a connecting element for forming a substance-to-substance bond with the outer shaft tube. The connecting element may comprise a metal ring molded into the injection molded body. The connecting element may be welded to the outer shaft tube. A corresponding embodiment of an endoscope provides a secure and hermetically sealed connection between the support body and the outer shaft tube.

BRIEF DESCRIPTION OF THE DRAWINGS

The embodiments are explained in more detail below with reference to some exemplary embodiments. In this regard, the illustrated embodiments are merely intended to contribute to a better understanding of the embodiments without limiting them, in which:

FIG. 2 illustrates a longitudinal sectional view of a shaft of an endoscope, and FIGS. 3a-3d illustrate cross-sectional views of a shaft of an endoscope.

DETAILED DESCRIPTION

Figure 1:
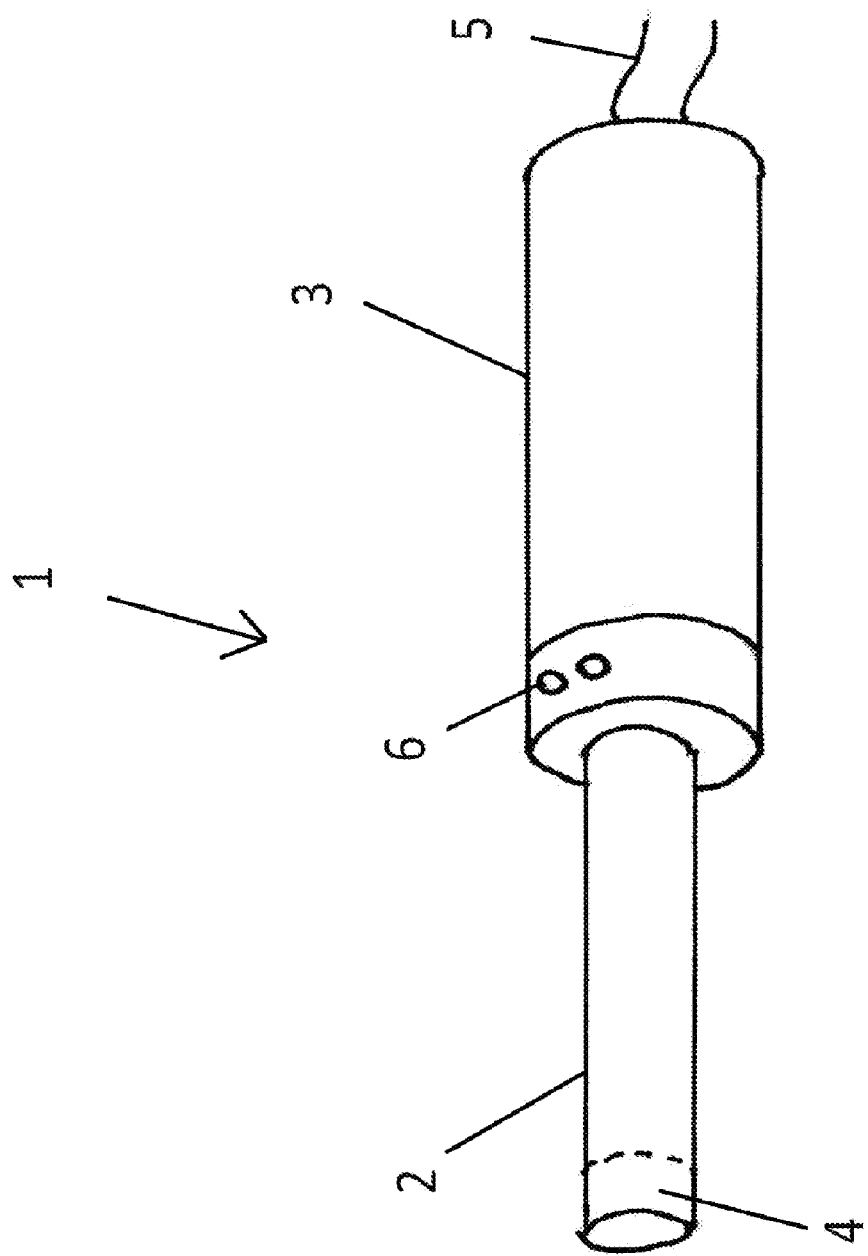
FIG. 1 illustrates an endoscope.

FIG. 1 shows an endoscope 1 with an elongated shaft 2 and a main body 3. An objective lens 4 is arranged in the distal end of the shaft 2, the image of which is converted into video signals by an electronic image sensor not shown.

The video signals from the image sensor are output, possibly after electronic preprocessing, via a cable 5.

Switches 6 are provided at the proximal end of the shaft 2, with which functions of the endoscope 1, a connected image processing unit, or further devices in a medical device system networked with the endoscope 1 can be controlled.

FIG. 2 shows the structure of the shaft 2. The shaft 2 comprises an inner shaft tube 10 in which an optical system 12 is arranged. A distal end of the inner shaft tube 10 is hermetically sealed by a window 13. The optical system 12 is shown here only cursorily, and may include a fiber optic image guide, a relay lens system, or a video camera, depending on the configuration of the endoscope 1.

The inner shaft tube 10 is received within an outer shaft assembly, which includes an outer shaft tube 15 and a tubular support body 16 proximally adjacent thereto. The support body 16 serves to connect the shaft 2 of the endoscope 1 to the main body 3.

Optical fibers 20 are laid in an annular space between the inner shaft tube 10 and the outer shaft tube 15, by means of which a field of view of the endoscope 1 can be illuminated. At the distal end of the shaft 2, the annular space is potted with adhesive so that the inner shaft tube 10, the outer shaft tube 15, and the optical fibers 20 form a unitary shaft assembly which is hermetically sealed distally by the window 13 and the adhesive.

In a proximal region of the shaft 2, the optical fibers 20 are grouped into one or more bundles (not shown in FIG. 2). These bundles are surrounded by a protective tube, not shown, which protects the sensitive optical fibers 20 from damage.

An electrical connecting element (connector) 25, which may be a flexible printed circuit board, is guided in an annular space between the inner shaft tube 10 and the support body 16. In the example shown, the electrical connecting element 25 serves to supply an electronic assembly 26, which is arranged outside the support body 16. For this purpose, the electrical connecting element 25 is guided through an opening 27 of the support body 16. The electronic assembly 26 may comprise the switches 6.

When assembling the shaft 2 of the endoscope 2, the bundles of optical fibers 20 must be prevented from colliding with the possibly sharp-edged electrical connecting element 25, since this could damage the protective tube and also the optical fibers 20 themselves.

FIGS. 3a to 3d show cross-sectional views of the shaft 2.

FIG. 3a shows a cross-section of the shaft 2 along the line A-A in FIG. 2. The inner shaft tube 10, the optical system 12, the outer shaft tube 15, as well as an annular space 30 filled with optical fibers 20 can be seen.

FIG. 3b shows a cross-section of the shaft 2 along the line B-B in FIG. 2. Again, the inner shaft tube 10 and the optical system 12 are shown. In addition, FIG. 3b shows the support body 16. In the example shown, the support body 16 has two webs 31, 32 at the location shown, each of which extends in a plane containing a longitudinal axis of the shaft 2. Thus, the webs 31, 32 extend, on the one hand, in the direction of the longitudinal axis of the shaft 2, and, on the other hand, radially to the longitudinal axis of the shaft 2. Furthermore, FIG. 3b shows how the electrical connecting element 25 is guided through the opening 27 of the support body 16.

The webs 31, 32 divide an annular space between the inner shaft tube 10 and the support body 16 into two segments 35a, 35b. In the respective segments 35a, 35b, the electrical connecting element 25 and the bundle of optical fibers 20 may be laid separately from each other so that mutual damage cannot occur during assembly.

In FIG. 3c, a cross-section of the shaft 2 is shown along the line C-C in FIG. 2. In this area, the support body 16 has a third web 33, which is shorter in the distal direction than the webs 31, 32, and is therefore not visible in FIG. 3b. The third web 33 divides the segment 35b of the annular space into two segments 35c, 35d. At the corresponding point of the shaft 2, the optical fibers are divided into two bundles 20, which are each guided separately through the segments 35c, 35d.

At the same time, the webs 31, 32, 33 guide the inner shaft tube 10 radially in the support body 16 and support the inner shaft tube 10 radially in the support body 16. This reduces the risk of forces occurring during assembly of the endoscope damaging the distal bonding of the optical fibers 20.

Instead of the three webs 31, 32, 33 shown, only two or more than three webs may also be provided. In this case, the annular space 35 is then divided into a number of segments corresponding to the number of webs.

FIG. 3d shows a cross-section of the shaft 2 along the line D-D in FIG. 2. In this area, the support body 16 is further widened so that more space is available to align the bundles of optical fibers 20 and to connect them to a light source or to another bundle of optical fibers. This may be, for example, a bundle of optical fibers in the cable 5 fixedly connected to the endoscope 1.

The support body 16 is made as an injection molded body of non-conductive plastic. This has the advantage that additional insulation of the electrical connecting element 25 is not required.

To enable a secure connection between the support body 16 and the outer shaft tube 15, a connecting element in the form of a metal ring 40 is integrated into the support body 16. The metal ring 40 is at least partially overmolded with the support body 16 and enables a substance-to-substance connection of the support body 16 to the outer shaft tube, for example by soldering or welding.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope comprising:
   an elongated shaft comprising:
      an inner shaft tube in which an optical system is received;

an outer shaft assembly comprising an outer shaft tube and a tubular support body proximally abutting the outer shaft tube;

at least one bundle of optical fibers disposed between the inner shaft tube and the outer shaft tube; and an electrical connector arranged between the inner shaft tube and the support body;

wherein the support body comprises at least a first web, a second web, and a third web, each extending radially between an inner surface of the support body towards an outer surface of the inner shaft tube, the first web, the second web, and third web also extending in a longitudinal direction of the shaft such that an annular space between the inner shaft tube and the support body is divided into at least three segments; and one of the first web, the second web and the third web is shorter in the longitudinal direction than the other of the first web, the second web and the third web such that two of the three segments converge to a common segment.

2. The endoscope according to claim 1, wherein the electrical connector is arranged in a first segment of the at least three segments.

3. The endoscope according to claim 1, wherein the electrical connector comprises one of a flexible printed circuit board and an electrical cable.

4. The endoscope according to claim 1, wherein the annular space between the inner shaft tube and the support body is in communication with a space between the inner shaft tube and the outer shaft tube at a distal end of the elongated shaft and the at least one bundle of optical fibers is arranged in a first segment of the three segments and extends distally to the space between the inner shaft tube and the outer shaft tube at a distal end of the elongated shaft.

5. The endoscope according to claim 1, wherein:
the at least one bundle of optical fibers comprises a first bundle of optical fibers and a second bundle of optical fibers, and
the electrical connector is arranged in a first segment of the three segments, the first bundle of optical fibers being arranged in a second segment of the three segments and the second bundle of optical fibers being arranged in a third segment of the three segments.

6. The endoscope according to claim 1, wherein the first web, the second web and the third web are configured to radially position the inner shaft tube.

7. The endoscope according to claim 1, wherein the support body is formed of plastic.

8. The endoscope according claim 1, wherein the support body comprises a connecting material formed of a metal material.

9. The endoscope according to claim 8, wherein the connecting material comprises a metal ring, other portions of the support body are formed of plastic and the metal ring is molded into the plastic support body.

10. The endoscope according to claim 9, wherein the outer shaft tube is formed of metal and the metal ring is welded to the outer shaft tube.

11. The endoscope according to claim 1, wherein at least one of the first web, the second web and the third web being configured to contact the outer surface of the inner shaft tube.

12. An elongated shaft for use with an endoscope, the shaft comprising:
an inner shaft tube in which an optical system is received; and
an outer shaft assembly comprising an outer shaft tube and a tubular support body proximally abutting the outer shaft tube;
wherein the support body comprises at least a first web, a second web, and a third web, each extending radially between an inner surface of the support body towards an outer surface of the inner shaft tube, the first web, the second web, and third web also extending in a longitudinal direction of the shaft such that an annular space between the inner shaft tube and the support body is divided into at least three segments; and
one of the first web, the second web and the third web is shorter in the longitudinal direction than the other of the first web, the second web and the third web such that two of the three segments converge to a common segment.

13. The elongated shaft according to claim 12, further comprising at least one bundle of optical fibers disposed between the inner shaft tube and the outer shaft tube.

14. The elongated shaft according to claim 13, wherein the at least one bundle of optical fibers is arranged in a second segment of the at least three segments.

15. The elongated shaft according to claim 12, wherein:
the at least one bundle of optical fibers comprises a first bundle of optical fibers and a second bundle of optical fibers, and
the electrical connector is arranged in a first segment of the three segments, the first bundle of optical fibers being arranged in a second segment of the three segments and the second bundle of optical fibers being arranged in a third segment of the three segments.

16. The elongated shaft according to claim 12, further comprising an electrical connector arranged between the inner shaft tube and the support body.

17. The elongated shaft according to claim 16, wherein the electrical connector is arranged in a first segment of the three segments.

* * * * *